(12) United States Patent
Vaeth

(10) Patent No.: US 10,046,326 B2
(45) Date of Patent: Aug. 14, 2018

(54) BIOREACTOR SUSPENSION

(71) Applicant: PATEFFECT SCHUTZRECHTSMANAGEMENT GBR, Aalen (DE)

(72) Inventor: Hans Vaeth, Messel (DE)

(73) Assignee: PatEffect Schutzrechtsmanagement GbR, Aalen (DE)

( * ) Notice: Subject to any disclaimer, the term of this patent is extended or adjusted under 35 U.S.C. 154(b) by 247 days.

(21) Appl. No.: 14/763,298

(22) PCT Filed: Jan. 27, 2014

(86) PCT No.: PCT/IB2014/058584
§ 371 (c)(1),
(2) Date: Jul. 24, 2015

(87) PCT Pub. No.: WO2014/118690
PCT Pub. Date: Aug. 7, 2014

(65) Prior Publication Data
US 2015/0352554 A1 Dec. 10, 2015

(30) Foreign Application Priority Data
Jan. 29, 2013 (DE) .................. 10 2013 001 444

(51) Int. Cl.
C12M 1/00 (2006.01)
C12M 3/00 (2006.01)
(Continued)

(52) U.S. Cl.
CPC ............... *B01L 9/00* (2013.01); *C12M 21/02* (2013.01); *C12M 23/06* (2013.01); *C12M 23/22* (2013.01);
(Continued)

(58) Field of Classification Search
CPC ...... C12M 23/48; C12M 23/46; C12M 23/50; C12M 21/02; C12M 23/22
See application file for complete search history.

(56) References Cited

U.S. PATENT DOCUMENTS 5,772,887 A * 6/1998 Noah ....................... C02F 3/02
210/150
6,228,636 B1 * 5/2001 Yahiro .................. C12M 23/48
312/236
(Continued)

FOREIGN PATENT DOCUMENTS

AU 2006100045 A4 2/2006
CN 101597567 A 12/2009
(Continued)

OTHER PUBLICATIONS

English translation of CN 101597567, Xinxin Ma, 2009.*
(Continued)

*Primary Examiner* — Nathan A Bowers
(74) *Attorney, Agent, or Firm* — Laurence A. Greenberg; Werner H. Stemer; Ralph E. Locher

(57) ABSTRACT

A supporting device for a multiplicity of parallel, highly elongate bioreactor elements having an at least partially transparent wall of plastic, through which a microorganism-inoculated nutrient solution is conducted for producing biomass by photosynthesis, includes a plurality of stationary support pylons disposed along the bioreactor elements and horizontally spaced apart from one another. The expenditure on production and assembly is decreased by providing at least one carrying element running between at least two support pylons above the respective bioreactor elements to be carried. The carrying element is supported on the corresponding support pylons and the bioreactor elements to be carried are connected to at least one carrying element by at (Continued)

least one holding element at least at one support point situated between the two support pylons.

18 Claims, 2 Drawing Sheets

(51) Int. Cl.
  *B01L 9/00* (2006.01)
  *C12M 1/12* (2006.01)
(52) U.S. Cl.
  CPC ............ *C12M 23/46* (2013.01); *C12M 23/48* (2013.01); *C12M 23/50* (2013.01)

(56) References Cited

U.S. PATENT DOCUMENTS

| | | | |
|---|---|---|---|
| 9,040,283 B2 | 5/2015 | Muller-Feuga | |
| 2004/0259239 A1* | 12/2004 | Branson | C12M 21/02 435/292.1 |
| 2007/0155006 A1* | 7/2007 | Levin | C12M 21/02 435/292.1 |
| 2007/0269888 A1* | 11/2007 | Houtzager | B01F 11/0017 435/252.1 |
| 2008/0131960 A1* | 6/2008 | Belongia | C12M 23/26 435/296.1 |
| 2010/0159579 A1 | 6/2010 | Schuring et al. | |
| 2014/0315290 A1* | 10/2014 | Mottahedeh | C12M 21/02 435/288.7 |
| 2015/0329810 A1* | 11/2015 | Wyatt | C12M 21/02 435/292.1 |

FOREIGN PATENT DOCUMENTS

| | | |
|---|---|---|
| DE | 19814253 A1 | 10/1998 |
| DE | 102004007564 A1 | 9/2005 |
| DE | 102013001444 A1 | 7/2014 |
| EP | 0402496 A1 | 12/1990 |
| WO | 2005079560 A1 | 9/2005 |
| WO | 2010109108 A1 | 9/2010 |
| WO | 2014118690 A1 | 8/2014 |

OTHER PUBLICATIONS

Cooper Industries Product Catalogue, www.cooperindustries.com/content/dam/public/bline/Resources/Library/catalogs/pipe_hangers/pipe_hangers_and_supports/Hangers.pdf, 2011.*
WayBack Machine search for www.cooperindustries.com/content/dam/public/bline/Resources/Library/catalogs/pipe_hangers/pipe_hangers_and_supports/Hangers.pdf, 2011.*

* cited by examiner

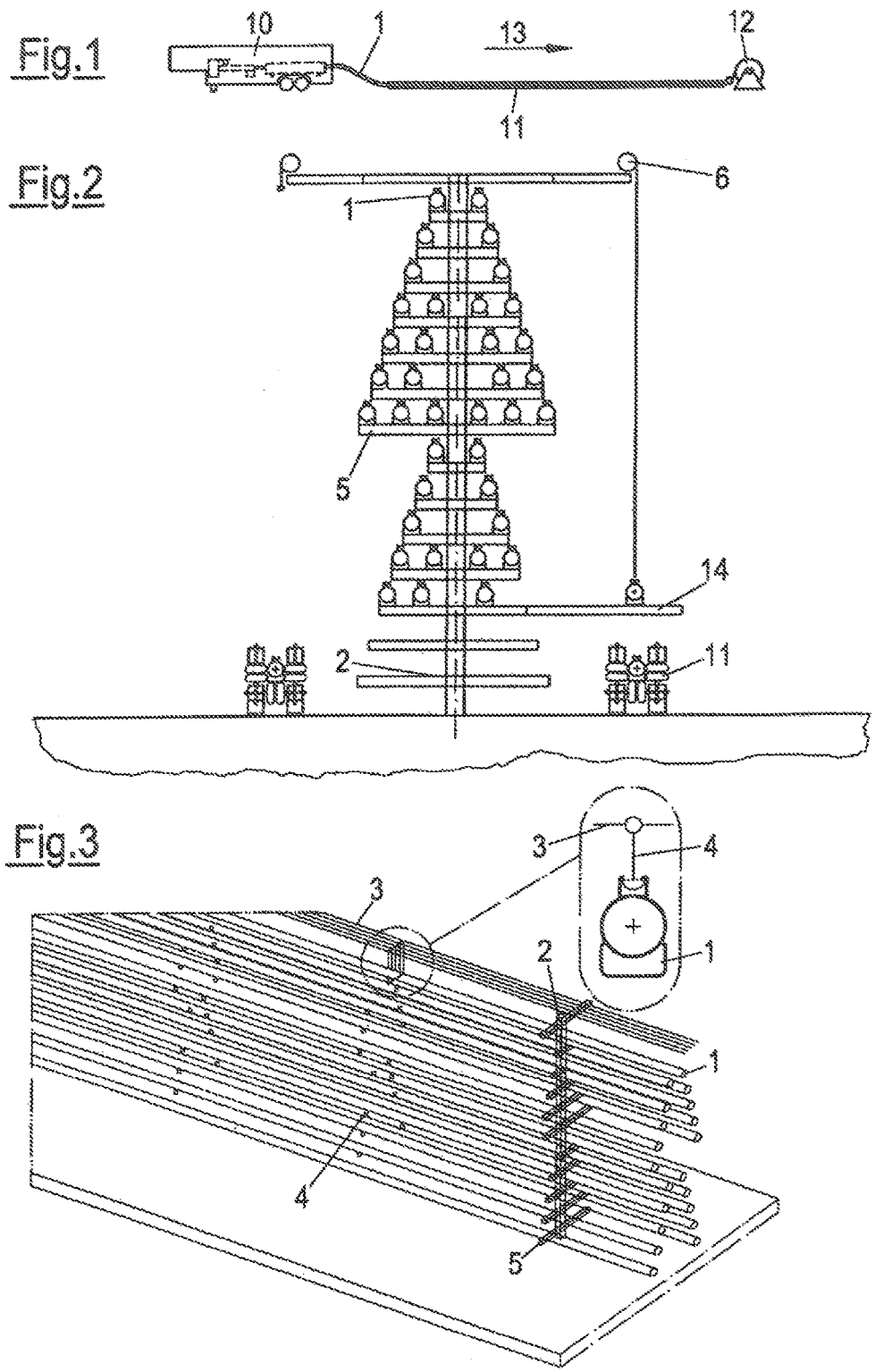

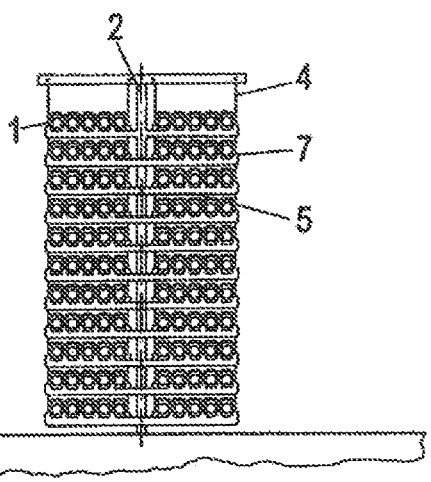
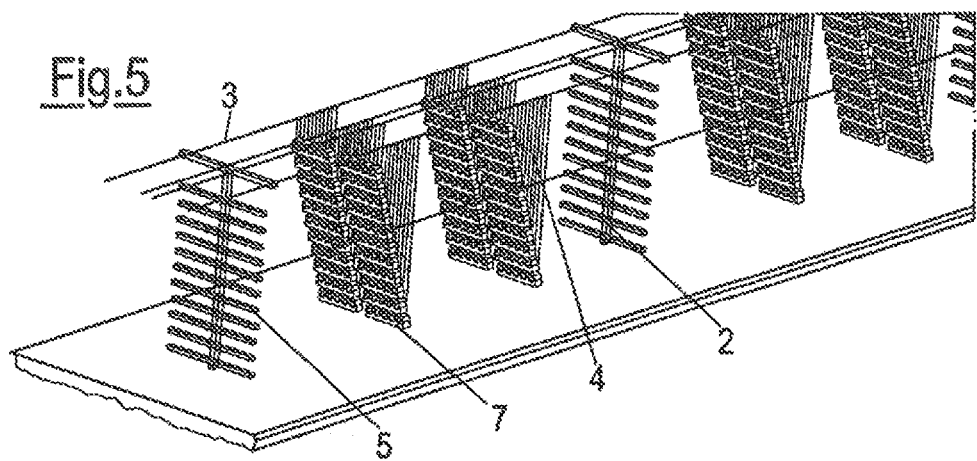
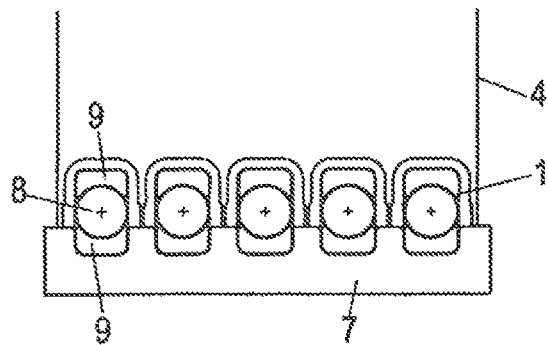

BIOREACTOR SUSPENSION

RELATED APPLICATIONS

This application is the U.S. National Phase under 35 U.S.C. § 371 of International Application No. PCT/IB2014/058584, filed Jan. 27, 2014, which in turn claims the benefit of German Application No. 102013001444.1, filed on Jan. 29, 2013, the disclosures of which Applications are incorporated herein.

BACKGROUND OF THE INVENTION

Field of the Invention

The invention relates to a supporting device for a multiplicity of highly elongate bioreactor elements running in parallel and approximately horizontally and having an at least partially transparent wall of plastic, through which a nutrient solution inoculated with microorganisms is conducted for producing biomass by means of photosynthesis, having a plurality of stationary supporting pylons arranged along the bioreactor elements and horizontally spaced apart from one another.

The production of biomass by means of photosynthesis has been known for some considerable time and is described inter alia in DE 198 14 253.

Increasingly used for this are closed systems in the form of tube reactors, which are irradiated with sunlight or artificial light directly or indirectly by way of light guiding systems.

In closed systems, the process conditions such as nutrient content, temperature, light intensity and $CO_2$ supply can be controlled much more precisely than in open arrangements.

In the interests of a low-cost construction, the transparent tubes or flexible hoses are usually laid horizontally here.

When scaling up to large plants, reliable support and guidance of the highly elongate bioreactor elements is found to require a relatively great effort.

BRIEF SUMMARY OF THE INVENTION

The object of the invention is therefore to reduce the effort involved in the production and assembly of such supporting devices.

The object has been achieved according to the invention by at least one carrying element running between at least two supporting pylons, over the bioreactor elements respectively to be carried, which carrying element is supported on the corresponding supporting pylons and the bioreactor elements to be carried are connected to at least one carrying element by way of at least one holding element at at least one supporting point lying between the two supporting pylons.

Creating supporting points between the supporting pylons allows the distance between the supporting pylons to be increased considerably, which has corresponding effects on the required number, and consequently also on costs.

Therefore, the invention provides its particular cost advantages when the substantially horizontally running bioreactor elements have a length of over 25, preferably over 50 and in particular over 100 m. It is entirely sufficient for this purpose if the distance between two neighboring supporting pylons is at least 3, preferably at least 6 m and/or the distance between two neighboring supporting points is at least 1, preferably at least 2 m.

In order to simplify the production and assembly of the bioreactor elements, they should in each case be formed in one piece. Here it is advantageous if the bioreactor elements are produced in the vicinity of their place of use with the aid of a mobile production unit.

The supporting of the bioreactor elements takes place at the supporting points indirectly by way of the holding elements and the carrying elements on the neighboring supporting pylons. This advantage becomes clear in particular whenever the carrying element is formed in its simplest form by a flexible supporting cable, supporting band or the like, running between the supporting pylons, and the holding elements are formed by simple hooks.

Apart from the supporting points, the bioreactor elements should additionally be supported directly on the supporting pylons, preferably on supporting arms fastened to the supporting pylons.

Because of the great linear dimensions of the bioreactor elements that are desired here, they are usually brought into position on the ground at the beginning of assembly. In order to facilitate the final positioning, it is of advantage if the supporting pylons have lifting devices suitable for bringing the bioreactor elements to the intended height, in particular into the region of the corresponding supporting arm.

In this case, assembly can be further facilitated by the supporting arms being extendable into the lifting region of the lifting devices. When the bioreactor elements are in their final position on the supporting arms, the supporting arms can be retracted again.

Furthermore, it is advantageous if the extent of the holding elements is variable. This allows not only raising of the bioreactor elements by way of the holding elements themselves, but also a readjustment of the position of the bioreactor elements by an extension or retraction of the corresponding holding element.

Depending on the number and weight of the bioreactor elements, it may be advantageous if a carrying element runs over each bioreactor element. In order to limit the effort involved in this respect, it is similarly of advantage if a plurality of bioreactor elements are respectively fastened to at least one carrying element, preferably all of the carrying elements.

To facilitate the fastening of the bioreactor elements to the holding elements, the bioreactor elements should have grooves, eyelets or the like in the region of the supporting points, for connection to the corresponding holding element.

Alternatively, however, it is also possible that a plurality of neighboring bioreactor elements are connected to one another in the region of at least one supporting point by way of a coupling element in each case, and the coupling element is fastened to one or more carrying elements by way of one or more holding elements.

In the interests of extensive support, the carrying elements should extend at least almost over the entire length of the bioreactor elements.

A particularly compact and simple construction can be achieved in this case by the bioreactor elements being arranged in a plurality of rows that lie one above the other and preferably run horizontally.

In this case, at least one, preferably each, row of bioreactor elements running on one side of the supporting pylons should be supported on a supporting arm in each case of the supporting pylons.

The invention is to be explained in more detail below on the basis of a plurality of exemplary embodiments.

BRIEF DESCRIPTION OF THE SEVERAL VIEWS OF THE DRAWING

In the appended drawing:

FIG. 1 shows an installation for producing very long bioreactor elements 1;

FIG. 2 shows a cross section through a supporting device;

FIG. 3 shows a longitudinal representation of the supporting device according to FIG. 2;

FIG. 4 shows a cross section through another supporting device;

FIG. 5 shows a longitudinal representation of the supporting device according to FIG. 4 and FIG. 6 shows a representation of a detail of the coupling element 7 according to FIGS. 4 and 5.

DESCRIPTION OF THE INVENTION

The horizontally running bioreactor elements 1 serve for the production of phototropic organisms and cell cultures under exposure to light, for which reason these elements are produced from an entirely or partially transparent plastic.

Particularly suitable for the production of very long, one-piece bioreactor elements 1 is the extrusion process, in which a solid to viscous and curable compound is continuously forced under pressure out of a shaping die of the extruder 10. In this way, complex structures can be formed and soft and brittle materials can be processed.

Because of the extensive possibilities for use, the extrusion compound used for producing the bioreactor elements 1 is formed here by thermoplastic material, in particular PMMA, PC, PE, PET or PVC.

After leaving the die, the plastic solidifies in a downstream, usually water-cooled calibrating unit of the extruder 10.

For the forming of tube or profile elements, the calibrating unit often has a calibrating sleeve, which serves for maintaining the form of the bioreactor element 1. In this case, the bioreactor element 1 is sucked against the inner wall of the calibrating sleeve by a vacuum. If the bioreactor element 1 has one or more channels 8, 9, these may also be closed in an airtight manner at the end leaving the extruder 10. It is thus possible to generate a positive air pressure inside the channels 8, 9 during the production of the bioreactor element 1 from the extrusion die of the extruder 10, and thus support the bioreactor element 1 from the inside. This may be necessary in particular in the case of the production of bioreactor elements 1 with low intrinsic stability.

The calibrating unit is generally also followed by a take-off device of the extruder 10, which transports the bioreactor element 1 out of the extruder 10, for example by way of running surfaces that move in the transporting direction and are pressed against the bioreactor element 1.

In order to avoid the transporting problems encountered with very long bioreactor elements 1 and facilitate the production of very long bioreactor elements 1, in particular also with a plurality of channels 8, 9, their production is performed in the direct vicinity of their place of use.

Outside the extruder 10, a tensile force acts here on the end leaving the extruder 10 and pulls the beginning of the bioreactor element 1 away from the extruder 10.

In this way, bioreactor elements 1 with a length of over 25 m or even over 50 m can be produced without any problem and at low cost. The one-piece production of great lengths avoids the sealing problems that arise when individual segments are joined together.

In this case, the distance after the extruder 10, i.e. also after the take-off device, can be used for cooling the bioreactor element 1.

In order that the extruder 10 can be used extensively in spite of production on site, it should be of a mobile design. For this purpose it is appropriate to mount the extruder 10 on a truck, from the loading area of which the beginning of the bioreactor element 1 is then pulled away. As a result, the pulling of the bioreactor element 1 should bring it as close as possible to the place of installation.

In order to be able to transfer the tensile force to the end leaving the extruder 10, fastened to this end there is for example a coupling piece, which is connected by way of a cable to a cable winch acting as a pulling device 12.

To avoid overstretching or even damaging the element 1 as a result of excessive forces, the tensile force is applied by a pulling device 12 of which the tensile force and/or position can be varied.

In the interests of lowest possible stressing of the bioreactor element 1 as a result of friction, it is supported during production between the extruder 10 and the beginning of the bioreactor element 1 on a guiding device 11, which, as represented in FIG. 1, extends over the entire length of the finished bioreactor element 1.

For this purpose, the guiding device 11 has distributed over the entire length a multiplicity of rotating guiding elements in the form of guiding rollers.

These guiding rollers support the bioreactor element 1 from below and also guide it on both sides with respect to the pulling direction 13.

This allows the end of the bioreactor element 1 that is leaving the extruder 10 to be pulled by the cable of the pulling device 12 in the guiding device 11 up to the end position.

In order to be able to produce as much biomass as possible, the installation comprises a multiplicity of highly elongate bioreactor elements 1 running in parallel and having an at least partially transparent wall of plastic, through which a nutrient solution inoculated with microorganisms is conducted for producing biomass by means of photosynthesis.

In order that the effort involved in bearing the bioreactor elements 1 is kept within limits, the corresponding supporting device for these bioreactor elements 1 is formed by a plurality of stationary supporting pylons 2 arranged along the bioreactor elements 1 and horizontally spaced apart from one another.

Carrying elements 3 run between the supporting pylons 2, over the bioreactor elements 1 respectively to be carried, are supported on the corresponding supporting pylons 2 and are connected to the bioreactor elements 1 to be carried by way of at least one holding element 4 at at least one supporting point lying between two neighboring supporting pylons 2.

In this way, the distance between the supporting pylons 2 can be very great without the support of the bioreactor elements 1 being adversely affected.

Even in the case of bioreactor elements 1 with a length of 50 m or more, it is sufficient if the distance between two neighboring supporting pylons 2 is at least 6 m and the distance between two neighboring supporting points is at least 1 m.

The carrying elements 3 extend almost over the entire length of the bioreactor elements 1 and are formed here by way of example by a flexible steel cable.

As indicated in FIG. 6, the holding elements 4 may be formed so as to be variable in length, or else quite simply as hooks.

Such a supporting construction involves not only low costs but also little assembly effort.

Apart from the indirect support by way of the carrying elements 3 and holding elements 4, the bioreactor elements 1 are also supported directly on the supporting pylons 2, in particular on supporting arms 5 fastened to the supporting pylons 2.

For an arrangement that is as compact as possible, the bioreactor elements 1 are arranged in a plurality of rows that lie one above the other and run horizontally. In this case, each row of bioreactor elements 1 running on one side of the supporting pylons 2 is supported on a supporting arm 5 in each case of the respective supporting pylons 2.

In order to facilitate a connection of the carrying elements 3 to the bioreactor elements 1, the bioreactor elements 1 according to FIGS. 2 and 3 may have grooves, eyelets or the like in the region of the supporting points.

Furthermore, FIG. 2 also shows supporting pylons 2 each with a lifting device 6 suitable for bringing the bioreactor elements 1 to the intended height, in particular into the region of the corresponding supporting arm 5.

In order that, during assembly, the bioreactor elements 1 can be easily pushed onto the corresponding supporting arm 5 after reaching the required height, the supporting arms 5 are extendable into the lifting region of the lifting devices 6 by means of an attachment 14.

Depending on the load-bearing capacity, each bioreactor element 1 may be assigned a carrying element 3 of its own, or a plurality of bioreactor elements 1 may be assigned one or more shared carrying elements 3.

In the case of the configuration according to FIGS. 4 to 6, a plurality of neighboring bioreactor elements 1 are connected to one another in the region of the supporting points by way of a coupling element 7 in each case. The coupling elements 7 are in turn fastened to two carrying elements 3 by way of two holding elements 4 in each case.

In their simplest configuration, the bioreactor elements 1 have only one channel 8 for the nutrient solution.

To create optimum temperature conditions, however, it may be necessary that, apart from the main channel 8, the bioreactor elements 1 also comprise, as in FIGS. 2 and 3, one cooling channel 9 or else, according to FIGS. 4 to 6, a plurality of cooling channels 9—here two.

By means of extrusion processes, bioreactor elements 1 having a plurality of cooling channels 9 can also be produced in one piece.

The invention claimed is:

1. A supporting device for a multiplicity of parallel, highly elongate bioreactor elements having an at least partially transparent wall of plastic, through which a microorganism-inoculated nutrient solution is conducted for producing biomass by photosynthesis, the supporting device comprising:
a plurality of stationary supporting pylons disposed along the multiplicity of parallel, highly elongate bioreactor elements, each of said supporting pylons being horizontally spaced apart from every other one of said supporting pylons and defining at least one supporting point disposed between two of said supporting pylons;
supporting arms fastened to said supporting pylons, the bioreactor elements being supported directly on said supporting arms;
said supporting pylons having lifting devices with a lifting region, said lifting devices being configured to bring the bioreactor elements to an intended height in a region of a corresponding supporting arm;
said supporting arms being extendable into said lifting region of said lifting devices;
at least one carrying element running between at least two of said supporting pylons above the bioreactor elements to be carried, said at least one carrying element being supported on said supporting pylons; and
at least one holding element connecting the bioreactor elements to be carried to said at least one carrying element at said at least one supporting point.

2. The supporting device according to claim 1, wherein said supporting pylons have lifting devices configured to bring the bioreactor elements to an intended height.

3. The supporting device according to claim 1, wherein said holding elements have a variable extent.

4. The supporting device according to claim 1, wherein said at least one carrying element includes a plurality of carrying elements each running over a respective one of the bioreactor elements.

5. The supporting device according to claim 1, wherein a plurality of the bioreactor elements are fastened to said at least one carrying element.

6. The supporting device according to claim 1, wherein said at least one carrying element includes a plurality of carrying elements, and a plurality of the bioreactor elements are fastened to all of said carrying elements.

7. The supporting device according to claim 1, wherein the bioreactor elements have grooves or eyelets in a region of said supporting points for connection to a corresponding holding element.

8. The supporting device according to claim 1, which further comprises a coupling element interconnecting a plurality of neighboring bioreactor elements in a region of said at least one supporting point, said coupling element being fastened to said at least one carrying element by said at least one holding element.

9. The supporting device according to claim 1, wherein said at least one carrying element extends at least almost over an entire length of the bioreactor elements.

10. The supporting device according to claim 1, wherein the bioreactor elements are disposed in a plurality of rows lying one above the other.

11. The supporting device according to claim 10, wherein said rows run horizontally.

12. The supporting device according to claim 10, wherein said supporting pylons have sides and supporting arms, and at least one of said rows of the bioreactor elements running on one of said sides of said supporting pylons is supported on a respective one of said supporting arms.

13. The supporting device according to claim 1, wherein the bioreactor elements have a length of over 25 meters, each two neighboring supporting pylons are spaced apart by a distance of at least 3 meters and each two neighboring supporting points are spaced apart by a distance of at least 1 meter.

14. The supporting device according to claim 1, wherein the bioreactor elements have a length of over 100 meters, each two neighboring supporting pylons are spaced apart by a distance of at least 6 meters and each two neighboring supporting points are spaced apart by a distance of at least 2 meters.

15. The supporting device according to claim 1, wherein the bioreactor elements are each formed in one piece.

16. The supporting device according to claim 1, wherein said at least one carrying element is formed as a flexible supporting cable or a supporting band.

17. The supporting device according to claim 1, wherein said supporting pylons are all disposed in a single row.

18. The supporting device according to claim 1, wherein said supporting pylons are all identical.

\* \* \* \* \*